(12) United States Patent
Dietze

(10) Patent No.: US 8,097,148 B2
(45) Date of Patent: Jan. 17, 2012

(54) METHOD FOR ULTRASONIC CLEANING OF A WORKING ELECTRODE IN ELECTROCHEMICAL CELL USEFUL FOR AUTOMATED TRACE METALS MEASUREMENT

(75) Inventor: William T. Dietze, Seattle, WA (US)

(73) Assignee: TraceDetect, Inc., Seattle, WA (US)

( * ) Notice: Subject to any disclaimer, the term of this patent is extended or adjusted under 35 U.S.C. 154(b) by 1087 days.

(21) Appl. No.: 11/617,510

(22) Filed: Dec. 28, 2006

(65) Prior Publication Data

US 2008/0017523 A1   Jan. 24, 2008

Related U.S. Application Data

(63) Continuation of application No. PCT/US2005/023347, filed on Jul. 1, 2005.

(60) Provisional application No. 60/584,876, filed on Jul. 1, 2004.

(51) Int. Cl.
*G01N 27/38* (2006.01)
(52) U.S. Cl. ............ 205/789.5; 204/402; 204/434; 205/775
(58) Field of Classification Search ............ 205/775, 205/789.5; 204/402, 434
See application file for complete search history.

(56) References Cited

U.S. PATENT DOCUMENTS

| 4,007,982 A * | 2/1977 | Stange ............ 399/351 |
| 4,033,830 A | 7/1977 | Fletcher, III |
| 4,814,197 A | 3/1989 | Duffy |
| 6,426,794 B1 * | 7/2002 | Trainoff ............ 356/246 |

FOREIGN PATENT DOCUMENTS

EP   0608037 A2   7/1994

OTHER PUBLICATIONS

Belmont et al, Analytica Chimica Acta 329, pp. 203-214, 1996.*
Edberg, H., et al., "Determination of Metals in Aqueous Solutions Using Nano-Band Electrodes," Proceedings of the Annual ISA Analysis Division Symposium 428:291-299, 2002.

* cited by examiner

Primary Examiner — Kaj K Olsen
(74) Attorney, Agent, or Firm — Christensen O'Connor Johnson Kindness PLLC

(57) ABSTRACT

Methods for cleaning and regenerating a working electrode in an electrochemical cell; method for measuring the concentration of a metal in a liquid sample in an electrochemical cell having a working electrode, the method including a step for cleaning and/or regenerating the electrode; and an assembly having an ultrasonic device in sonic communication with an electrochemical cell.

18 Claims, 2 Drawing Sheets

METHOD FOR ULTRASONIC CLEANING OF A WORKING ELECTRODE IN ELECTROCHEMICAL CELL USEFUL FOR AUTOMATED TRACE METALS MEASUREMENT

CROSS-REFERENCES TO RELATED APPLICATIONS

This application is a continuation of International Patent Application No. PCT/US2005/023347, filed Jul. 1, 2005, which claims the benefit of U.S. Provisional Application No. 60/584,876, filed Jul. 1, 2004, each application which is hereby incorporated herein by reference in its entirety.

BACKGROUND OF THE INVENTION

There are many methods by which trace metals can be measured. Techniques that are useful for measuring trace metals in aqueous solutions include colorimetric methods, atomic absorption (AA) methods, inductively-coupled plasma (ICP) methods, X-ray fluorescence (XRF) methods; ion-selective electrode (ISE) methods, and stripping voltammetry (ASV, CSV, and PSA) methods.

Colorimetric measurements are useful when the concentration of the metal is relatively high (generally greater than 1 ppm) and are prone to interferences from common salts, sulfates, and other dissolved inorganic compounds. ISE methods are also not practical for ppb level measurements, particularly in solutions with many other metals present. XRF methods used in the field are useful at concentrations of 10 ppm and above. Although AA, ICP and laboratory-based XRF methods have each been used for the reliable measurement of trace metals below 1 ppb, only stripping voltammetry is suitable for unattended operation. The barriers to using AA, ICP, and XRF methods for these analyses are immense and include the expense to implement and the requirement for intensive support infrastructure.

Of the electrochemical methods, stripping voltammetry is the more sensitive. Stripping voltammetry takes place in either a two- or three-electrode electrochemical cell, which includes at least a working electrode and a reference electrode. The optional third electrode is called the "counter" or the "auxiliary" electrode. The auxiliary electrode is used when either the reference electrode has high internal electrical resistance or the solution has high resistivity. In either case, the auxiliary electrode is used in conjunction with a potentiostat to help compensate for parasitic voltage drops that appear across the electrical resistances in the measurement circuit.

Stripping voltammetry follows a conceptually simple procedure: (optionally) electrochemically clean the working electrode; setting the voltage on the working electrode (with respect to the reference electrode) to a deposition potential and accumulating the target analyte on the tip of the working electrode; ramping the working electrode voltage such that the deposited analyte is removed (stripped) by electrochemical reactions mediated by the working electrode and its potential.

While ramping the working electrode voltage, the electrical current that flows to the working electrode is measured and recorded. The presence of the target analyte, and in particular, the stripping of the analyte can be detected, monitored, and quantified through the measured current. The "ramp" function can be a linear increase (or decrease) with respect to time, it can be a staircase (digital) ramp, or it can take on a more complicated waveform such as in square wave stripping in which a periodic square wave voltage in added to the linear or digital ramp function.

Ultrasonic cleaning techniques are well known and ultrasonic techniques have been combined with stripping voltammetry for the purposed of in situ enhancement of the sensitivity and to keep the electrodes involved in the measurement clean. In-place sonication of electrodes have been described in U.S. Pat. Nos. 4,033,830 and 4,786,373. These patents describe the cleaning of electrodes for amperometric measurements and the direct ultrasonic excitation of the working electrode during the measurement. A considerable body of work concerning the use of ultrasound to enhance sensitivity of a trace metals measurement made via stripping voltammetry and to keep the electrode clean during a stripping voltammetry measurement in a sample that would otherwise foul the electrode sensing surface can be found in various scientific papers by Compton et al. A representative example summary of this work can be found in "Sonoelectroanalysis—an overview" by A. J. Saterlay and R. G. Compton, *Fresenius J. Anal. Chem.* 367:308-313 (2000).

A need exists for a practical, low-cost method for automatically monitoring trace metals in solution. Although several technologies exist for measuring trace metals, these methods are not very sensitive (they measure metals at non-trace concentrations) and are very expensive. None of the technologies offers the prospect of affordable long-term, unattended operation. The present invention seeks to fulfill this need and provides further related advantages.

SUMMARY OF THE INVENTION

In one aspect, the present invention provides a method for regenerating or cleaning a working electrode in an electrochemical cell. In the method, ultrasonic energy is applied to a working electrode in an electrochemical cell, the electrode having a surface that is fouled by accumulated material thereby reducing the electrode's effectiveness, wherein the applied ultrasonic energy is sufficient to remove at least a portion of the accumulated material from the surface thereby cleaning the surface and regenerating the electrode.

In another aspect of the present, a method for regenerating a working electrode in an electrochemical cell is provided. The method includes the steps of applying ultrasonic energy to a working electrode in an electrochemical cell, wherein the electrode has a surface comprising a metal film plated thereon, wherein the metal film is fouled by accumulated material thereby reducing the electrode's effectiveness, wherein the applied ultrasonic energy is sufficient to remove at least a portion of the fouled metal film to provide to an electrode surface for receiving a metal; and plating a metal on the electrode surface for receiving a metal to provide a metal film on the electrode surface, thereby regenerating the working electrode.

In another aspect, the present invention provides a method for measuring the concentration of a metal in a liquid sample in an electrochemical cell. In the method, the metal concentration is measured for one or more samples sequentially by an electrochemical technique, such as stripping voltammetry, using a working electrode; after measuring the metal concentration for the sample or samples, the working electrode is cleaned or regenerated; and then after the electrode has been cleaned or regenerated, analysis of one or more additional samples is continued. The method includes the steps of introducing a first liquid sample containing a measurable quantity of a metal into an electrochemical cell comprising a working electrode, the electrochemical cell suitable for measuring the concentration of the metal in the sample by stripping voltammetry; measuring the concentration of the metal in the first sample by stripping voltammetry; exiting the first liquid sample from the electrochemical cell; introducing a cleaning liquid (e.g., water) into the electrochemical cell; applying ultrasonic energy to the working electrode, wherein the applied ultrasonic energy is sufficient to remove at least a portion of accumulated material from the electrode surface thereby regenerating the electrode; introducing a second liquid sample containing a measurable quantity of a metal into the electrochemical; and measuring the concentration of the metal in the second sample by stripping voltammetry. In one embodiment, the electrode has a surface further comprising a metal film plated thereon; the applied ultrasonic energy is sufficient to remove at least a portion of the metal film to provide to an electrode surface for receiving a metal; and the method further comprises the step of plating a metal on the electrode surface for receiving a metal to provide a metal film on the electrode surface, thereby regenerating the working electrode.

In a further aspect, the invention provides an assembly comprising an ultrasonic device in sonic communication with an electrochemical cell. The ultrasonic device includes a housing; an ultrasound generator for generating ultrasonic energy; an ultrasonic window for coupling the ultrasonic energy into the flow cell; and a chamber defined by the housing, ultrasound generator, and ultrasonic window for receiving a liquid to provide a reservoir. The electrochemical cell includes a flow cell having a sample volume for receiving a liquid sample, the sample volume in communication with a sample inlet and sample outlet, wherein the sample volume is defined by the flow cell and the ultrasonic window; and a working electrode in liquid communication with the liquid sample for measuring the concentration of a metal in the liquid sample.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
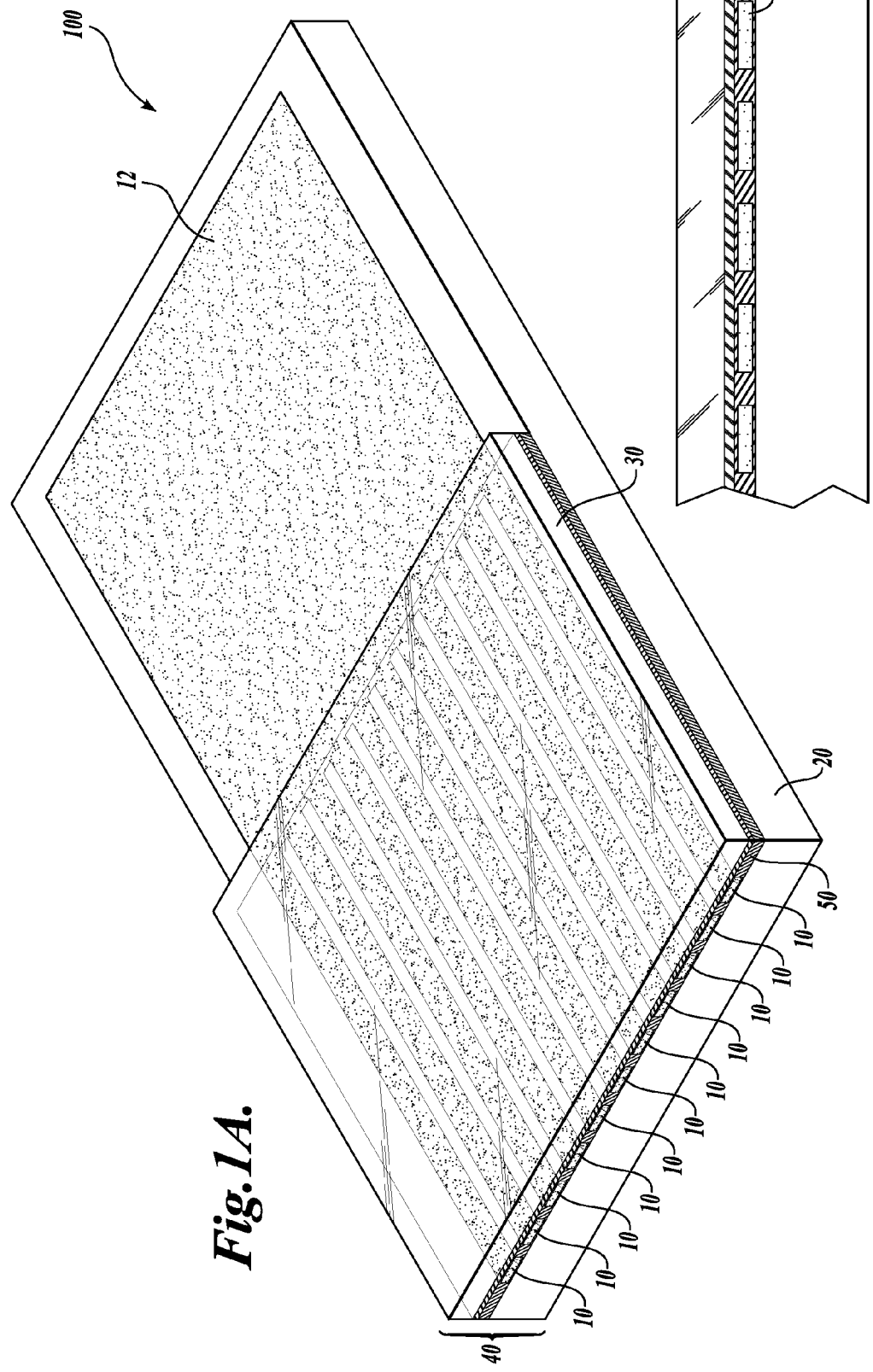
FIG. 1A is a schematic illustration of a representative a portion of an electrode (electrode array commercially available from TraceDetect, Seattle, Wash. under the designation NANO-BAND electrode), each sub-electrode of the electrode is buried in a layer of insulator ($SiO_2$, $Si_3N_4$, or other material), the electrode array is mounted in an electrode housing complete with electrical connector to provide the electrode.
FIG. 1B is a schematic illustration of a portion of the sensing surface of the electrode illustrated in FIG. 1A.

The present invention provides a device and method for cleaning and/or regenerating a working electrode in an electrochemical cell that is useful in automated trace metals measurement. In the method, electrode cleaning is achieved using ultrasonic cavitation.

The electrochemical cell is useful for measuring trace amounts of metals dissolved in solution. In one embodiment, the electrochemical cell is useful in trace metals measurement by the technique of stripping voltammetry. In the electrochemical cell, the working electrode is mounted in the cell and, through its operation, can become fouled.

In accordance with one aspect of the present invention, the fouled working electrode is cleaned by sonication in-place in the electrochemical cell using an ultrasonic transducer (i.e., ultrasonic generator). By the method of the invention, the useful lifetime of the working electrode is greatly extended. Extension of the electrode's useful life increases sample throughput and decreases the workload of the service personnel.

Thus, in one aspect, the present invention provides a method for regenerating or cleaning a working electrode in an electrochemical cell. In the method, ultrasonic energy is applied to a working electrode in an electrochemical cell, the electrode having a surface that is fouled by accumulated material thereby reducing the electrode's effectiveness, wherein the applied ultrasonic energy is sufficient to remove at least a portion of the accumulated material from the surface thereby cleaning the surface and regenerating the electrode.

In accordance with one another aspect of the present invention, a working electrode having a pre-plated thin metal film on the tip of the electrode is regenerated. Working electrodes include such thin films to modify the characteristics of the working electrode to increase its sensitivity, reliability, or to allow measurements not otherwise possible using the base electrode material. By the method of the invention, ultrasonic cleaning of such an electrode, aside from removing compounds that have built up on the surface of the electrode, can also effectively remove the fouled metallic thin-film. Removal of the fouled metallic thin film this is the most thorough cleaning of the electrode possible.

In the method, regeneration of the working electrode includes ultrasonic cleaning of the electrode, whereby most or all of the metallic-thin film is removed, followed by reapplication of the thin metal film by plating. In accordance with the method, these steps can be performed automatically in a measurement cell, allowing in-place regeneration of the electrode and long-term unattended operation of an instrument for trace metals measurement via stripping voltammetry.

Thus, in another aspect of the present, a method for regenerating a working electrode in an electrochemical cell is provided. The method includes the steps of applying ultrasonic energy to a working electrode in an electrochemical cell, wherein the electrode has a surface comprising a metal film plated thereon, wherein the metal film is fouled by accumulated material thereby reducing the electrode's effectiveness, wherein the applied ultrasonic energy is sufficient to remove at least a portion of the fouled metal film to provide to an electrode surface for receiving a metal; and plating a metal on the electrode surface for receiving a metal to provide a metal film on the electrode surface, thereby regenerating the working electrode.

In certain embodiments of the above methods, the electrode comprises gold, iridium, platinum, carbon, glassy carbon, or diamond.

In certain embodiments of the above methods, the metal film on the surface of the electrode comprises gold, bismuth, copper, silver, or mercury.

In certain embodiments of the above methods, the electrode is at least one of a disk electrode, a microelectrode, an electrode array of microelectrodes, or a printed electrode.

In the above methods, the electrode is suitable for measuring the concentrations of trace metals by amperometry, potentiometry, direct voltammetry, and cyclic voltammetry methods.

In certain embodiments of the above methods, the electrochemical cell is a flow cell.

In certain embodiments of the above methods, regenerating the electrode is performed intermediate measuring trace element concentrations using the electrode. The methods of the invention allow for automated trace metal analysis by virtue of the ability to perform one or more electrochemical analyses followed by electrode cleaning and/or regeneration, and then continued electrochemical analyses without removing the electrode from the electrochemical cell.

In the methods of the invention, the ultrasonic energy is applied through an ultrasonic window. In certain embodiments, the ultrasonic energy is generated by an ultrasonic horn. The ultrasonic generator (e.g., horn) is in sonic communication with the electrode through the ultrasonic window. In certain embodiments, the ultrasonic energy is applied in the megasonic frequency range.

The methods of the invention overcome existing problems for electrochemical trace metal measurement by stripping voltammetry. With the advent of the methods of the invention, electrochemical trace metal measurement by stripping voltammetry becomes practical and widely applicable. Potential stripping voltammetry applications include environmental monitoring in the field (e.g., monitoring lakes, streams, estuaries, ocean waters, and ground waters); industrial waste-water monitoring in order to comply with environmental regulation; industrial waste-water monitoring in order to recover metals used in an upstream process step; industrial process control where the metal concentration must be controlled as a key part of a process/manufacturing operation; industrial process control where metal contaminants must be reduced or eliminated in order to guarantee produce quality; monitoring of waste waters associated with mining and ore extraction; monitoring of food and drug manufacture in order to guarantee metals free product; monitoring of food and drug manufacture in order to improve quality and/or cosmetic appearance of the product or of its taste; monitoring of waste and natural waters for key controlled and indicator metals associated with the manufacture of nuclear materials.

Ultrasonic cleaning techniques are well known and ultrasonic techniques have been combined with stripping voltammetry for the purposed of in situ enhancement of the sensitivity and to keep the electrodes involved in the measurement clean. In-place sonication of electrodes have been described in U.S. Pat. Nos. 4,033,830 and 4,786,373. These patents describe the cleaning of electrodes for amperometric measurements and the direct ultrasonic excitation of the working electrode during the measurement.

In contrast to other known methods, the methods of the invention provides combining the ultrasonic cleaning of electrodes in an electrochemical cell for the express purpose of cleaning the working electrode as part of a reconditioning process, and not during the actual measurement. In the methods of the invention, ultrasonic cleaning of the working electrode in an electrochemical cell, which may be coated with a thin film of metal (typically either gold or mercury), is not carried out during the time when the measurement is being made. Rather, in accordance with the invention, the ultrasonic cleaning is an integral part of an electrode regeneration scheme by which the electrode is cleaned after use or, when the working electrode includes a thin metal film, the old thin metal film is removed (along with any contaminants built up on the surface of the thin film electrode or dissolved into in the bulk of the applied thin film) and a new thin-film is applied.

In one aspect, certain embodiments of the methods of the invention differ from other ultrasonic cleaning methods in that the method of the invention includes an ultrasonic cleaning step to remove, at least in part, the previously applied thin metal film, which can then be replaced with a fresh thin metal film.

One advantage in the in-place nature of the cleaning/regeneration method of the invention is that, without this ability, a fully automated and autonomous trace metals analysis instrument cannot be created. The method of the invention allows for a cleaning regimen that is non-contact. Because of the nature of trace elemental determinations, contamination from the cleaning process is always worrisome. In accordance with the method of the invention, sonic energy is projected through a wall (window joining electrochemical cell and ultrasonic device, see FIG. 2) in the assembly and no contamination can be introduced.

In another aspect, the present invention provides a method for measuring the concentration of a metal in a liquid sample in an electrochemical cell. In the method, the metal concentration is measured for one or more samples sequentially by an electrochemical technique, such as stripping voltammetry, using a working electrode; after measuring the metal concentration for the sample or samples, the working electrode is cleaned or regenerated; and then after the electrode has been cleaned or regenerated, analysis of one or more additional samples is continued. The method includes the steps of introducing a first liquid sample containing a measurable quantity of a metal into an electrochemical cell comprising a working electrode, the electrochemical cell suitable for measuring the concentration of the metal in the sample by stripping voltammetry; measuring the concentration of the metal in the first sample by stripping voltammetry; exiting the first liquid sample from the electrochemical cell; introducing a cleaning liquid (e.g., water) into the electrochemical cell; applying ultrasonic energy to the working electrode, wherein the applied ultrasonic energy is sufficient to remove at least a portion of accumulated material from the electrode surface thereby regenerating the electrode; introducing a second liquid sample containing a measurable quantity of a metal into the electrochemical; and measuring the concentration of the metal in the second sample by stripping voltammetry. In one embodiment, the electrode has a surface further comprising a metal film plated thereon; the applied ultrasonic energy is sufficient to remove at least a portion of the metal film to provide to an electrode surface for receiving a metal; and the method further comprises the step of plating a metal on the electrode surface for receiving a metal to provide a metal film on the electrode surface, thereby regenerating the working electrode.

The methods of the invention are applicable to a variety of electrochemical techniques including stripping voltammetry, among others.

Stripping voltammetry. The methods of the invention are particularly well suited for cleaning working electrodes useful trace metal measurement by stripping voltammetry. Representative stripping voltammetry methods that benefit from the methods of the invention include anodic stripping voltammetry and cathodic stripping voltammetry.

Anodic stripping voltammetry (ASV) is a type of stripping voltammetry in which the working electrode is made anodic (more positive) with respect to the reference electrode during the optional cleaning step, the working electrode is made more cathodic (more negative) during the deposition step, and the stripping takes place when the working electrode is anodically ramped (the ramped voltage applied to the working electrode ends up at a more positive than it's starting voltage). ASV is most often used to measure directly-platable metals in solution such as zinc, copper, cadmium, lead, arsenic, mercury, thallium, tin, antimony, and bismuth.

Cathodic stripping voltammetry (CSV) is a type of stripping voltammetry in which the working electrode is made cathodic (more negative) with respect to the reference electrode during the optional cleaning step, the working electrode is made more anodic (more positive) during the deposition step, and the stripping takes place when the working electrode is cathodically ramped (the ramped voltage applied to the working electrode ends up at a more negative than it's starting voltage). CSV is most often used to measure metals in solution via adsorptive techniques. Adsorptive techniques require an organic "complexing" agent that binds the target analyte. The complexing agent does this while adsorbed to the surface of the working electrode. The stripping action is the release of the bound analyte from the adsorbed organo-metallic complex. This technique can be used for almost all the transition metals in the periodic table as well as many other metallic and nonmetallic elements.

Other applicable electrochemical methods. In addition to the stripping voltammetry methods noted above, the methods of the invention are applicable to any electrochemical method that requires a special thin-film (for reasons of increasing sensitivity, selectivity or sensor range) to be applied to the working electrode. Measurements that could benefit include amperometry (measure the working electrode current at a fixed electrode voltage), potentiometry (measure the working electrode potential under conditions of zero or constant electrode current), direct voltammetry (this is stripping voltammetry performed without the plating step), and cyclic voltammetry (in which the working electrode voltage is ramped both positive and negative in a cyclic fashion).

The following types of electrodes are suitable for cleaning and/or regenerating in accordance with the methods of the invention.

Hanging mercury drop electrode. The classic electrode for voltammetry (as well as for stripping voltammetry) is the hanging mercury drop. Typical drop sizes are from about 0.1 mm to about 0.5 mm diameter and are suspended from a glass capillary. Because the mercury is liquid, this electrode cannot be mechanically cleaned. Fouling of hanging mercury drops can be due to adsorbed organics coating the surface of the electrode or inorganic materials that either build up on the surface of the electrode or build up as dissolved material in the mercury. In either case, a fouled hanging mercury drop is removed by knocking the drop off and forming another one by pushing more (fresh) mercury through the capillary tube from which the drop hangs. Ultrasonication has been used with hanging mercury drop electrodes, but only as a means to knock the old drop off, prior to its replacement with a new one.

Disk electrodes (macro electrodes with diameters>0.5 mm). The disk electrode is simply a rod of electrode material (e.g., carbon, gold, platinum) potted in an inert cladding material and end-polished. The result is a disc-shaped electrode in a planar structure, typically the surrounding material (epoxy or plastic) is a larger rod with the electrode mounted coaxially. These electrodes are used bare or with a thin film of plated metal. The term "thin-film" when applied to mercury thin-films is not meant to imply the formation of an actual film of mercury. The mercury "thin-film" is typically a collection of mercury balls (often of various sizes) plated on to the surface of the electrode disk.

Disk electrodes eventually foul and for the same reasons as the hanging mercury drop electrode: built up adsorbed organics or deposits of inorganic materials that interfere with the measurement. If the disc electrode uses a thin-film of mercury, then that mercury can be contaminated as well. The traditional solution to this problem is to polish (or buff) the disc on a pad with grit or to polish it with very fine sandpaper. This action removes the offending material and exposes fresh electrode material for new measurements.

Microelectrodes. Microelectrodes are typically very small disk electrodes. These electrodes differ in their utility as sensors, but differ little in terms of how they foul and in their need for reconditioning. These electrodes are polished and/or buffed as are disk electrodes. Microelectrodes can have various shapes. The term "ultra-microelectrodes" has been applied to microelectrodes with dimensions less than about 10 microns. Microelectrodes can also utilize thin-films of metal plated on to their active surface prior to measurement.

Printed electrodes. Printed electrodes use either screen-printing (electrode dimensions generally greater than a half-millimeter) or photolithography (electrodes as small as a one or two microns). If used in a planar fashion, that is, the surface on which the electrode is printed is the active surface of the electrode, these electrodes are hard to (or impossible to) mechanically clean. Polishing and/or buffing tends to remove the electrodes from the substrate upon which they are printed. These electrodes are sometimes "electrochemically" or "chemically" cleaned prior to use. However, these techniques can never fully restore the electrode surface to its original pristine condition. The utility of printed electrodes is generally limited to disposable applications so that cleaning after use is not required.

Electrode arrays. Electrode arrays, or linear arrays of microelectrodes (such as commercially available from Trace-Detect, Seattle, under the designation NANO-BAND), can be mechanically cleaned. The NANO-BAND electrode is a linear array of (rectangular) microelectrodes (e.g., 100 sub-electrodes connected electrically in parallel, see FIGS. 1A and 1B). The electrode array can be thought of as a single electrode for the purpose of making the measurement and ultrasonic cleaning occurs at the sub-electrode level. This electrode is printed, but not used in a planar fashion. The electrode is constructed in much the same way as a disk electrode. A schematic illustration of a representative electrode array is shown in FIG. 1A. Referring to FIG. 1A, representative electrode 100 includes a plurality of long thin sub-electrodes 10 emanating from contact pad 12, supported on substrate 20, and covered with sheet 30 (e.g., glass cover slip), which is end polished to provide sensing surface 40. The sensing surface is the cross-section of the printed electrode in a plane perpendicular to that of the printed surface. Sensing surface 40 is illustrated in FIG. 1B. Referring to FIG. 1B, sub-electrodes 10 are embedded in insulated (e.g., nitride) layer 50 intermediate substrate 20 and sheet 30, which is adhered to insulated layer 50 by adhesive (e.g., epoxy) layer 60.

Electrode Preparation. Typical electrode preparation prior to use removes any material that may have fouled the electrode. Electrode preparation also removes any oxides that may have built up while in storage. Because most electrodes are reused, this process is also termed "regeneration".

The following is an example of a typical polishing/buffing procedure for preparing an electrode. The electrode is buffed on a felt pad using a suspension of alumina grit (grit sizes from 0.05 micron to 5 microns) in water, the electrode tip is rinsed, the electrode is buffed again on a clean (grit free) felt pad to fully remove residual grit, and the electrode tip is rinsed again. If a thin film is to be used, then the film is deposited in the electrode. The electrode is ready for immediate use.

For electrode arrays (e.g., NANO-BAND electrodes), thin films of mercury or gold are deposited prior to stripping voltammetric measurements. Larger electrodes do not necessarily require this step for best operation. Once the plated thin metal film is deposited on the tip of the electrode, the electrode can be used until it fouls. The rate of fouling depends upon the measurement parameters, the metals measured, as well as exposure to air, the supporting electrolyte, and the sample itself. Thin film gold electrodes in very clean samples work well for over a week, while thin film mercury electrodes rarely operate for more than two days before fouling.

Electrochemical cell. The methods of the invention are applicable to electrochemical analyses using an electrochemical cell. Electrochemical cells include at least two electrodes: (a) a working electrode and (b) a reference electrode. Electrochemical cells may optionally include a third (e.g., auxiliary) electrode. Of the electrochemical methods, stripping voltammetry is the more sensitive. Stripping voltammetry takes place in either a two- or three-electrode electrochemical cell, which includes at least a working electrode and a reference electrode. The optional third electrode is called the "counter" or the "auxiliary" electrode. The auxiliary electrode is used when either the reference electrode has high internal electrical resistance or the solution has high resistivity. In either case, the auxiliary electrode is used in conjunction with a potentiostat to help compensate for parasitic voltage drops that appear across the electrical resistances in the measurement circuit.

The nature and type of electrodes useful in a particular electrochemical cell will vary and depend on the nature of the electrochemical analysis performed.

Ultrasonic cleaning method for electrodes. Mechanical cleaning (polishing and/or buffing) removes all built-up material and the plated metals from the tip of the electrode. Buffing with grit (or using fine sandpaper) also removes a small amount of electrode material as well (both glass, encapsulant, epoxy and the electrode material); exposing fresh electrode metal. Ultrasonic cleaning can also remove all built-up material and plated metals through the cleaning action of cavitation. When grit is added to the solution, and ultrasound applied, then the removal of electrode material (substrate, epoxy, and metal) also occurs. Note that at sufficiently high power, the cavitation effect can erode the electrode surface without the presence of grit. With or without grit, sufficiently strong ultrasonic energy is applied to the solution in which the electrode is immersed, electrode metal can be removed, recessing the electrode surface slightly. It is noted that this is to be avoided because recessed electrodes are harder to plate and harder to clean after use.

The ultrasound frequency has an effect on the ultrasonic cleaning action. Low frequencies (e.g., 20-40 kHz) produce a relatively smaller number of very energetic bubbles. These bubbles form during the low-pressure portion of the acoustic wave and collapse during the high-pressure portion of the acoustic wave. At low frequency, the bubbles have a relatively long time to form and, as a result, the bubbles become larger and their collapse is very energetic. High frequencies produce a larger number of bubbles, but their size is smaller given the same applied acoustic power. Thus, at high frequency the cavitation (bubble collapse) of each bubble is less energetic than those formed with low frequencies and is less effective for cleaning a surface. However, there are benefits of using higher ultrasonic frequencies. The use of higher ultrasonic frequencies with suitable applied power promotes cleaning of smaller features and the size of the (typically resonant) transducer is much smaller. At 30 kHz the acoustic wavelength in water is about 49 mm, while at 1.5 MHz (a typical "megasonic" frequency) the wavelength is reduced to about 1 mm. For titanium, a typical material used in resonant ultrasonic "horns", these wavelengths are increased by a factor of about 4 so half-wave resonators have wavelengths on the order of about 100 mm and about 2.0 mm, respectively.

Bath ultrasonic cleaning. Commercial "bath" type ultrasonic cleaners operate between 20 kHz and 40 kHz. In one embodiment, ultrasonic cleaners at 90 W, 2-liter bath operating at 40 kHz were effective in regeneration of a representative electrode array (e.g., NANO-BAND electrodes).

A representative method included the following steps:

1. Plating the electrode with a thin metal film and perform a square-wave measurement of current (on a anodic ramp) in a voltage region where no electrochemical reactions are expected to establish a "capacitive current" that is proportional to electrode surface area. For a gold electrode, a gold thin film can be plated. For a carbon or iridium electrode, either a mercury or gold thin film can be plated. Bismuth and other thin-film materials can be used as well.

2. Scanning the electrode with a staircase ramp in the appropriate supporting electrolyte blank (no metals) in order to measure the background currents (same scan parameters used for a typical trace metals measurement). For a mercury thin film electrode, representative scanning parameters include scanning from about −1300 mV to about +200 mV (with respect to a Ag/AgCl reference electrode) in a 0.1 M acetate buffer solution. For a gold thin film electrode, representative scanning parameters include scanning from about −400 mV to about +650 mV (with respect to a Ag/AgCl reference electrode) in a 0.2 to 2.0 M solution of HCl.

3. Immersing the electrode in the ultrasonic cleaner for from about 3 to about 15 minutes.

4. Visually inspect the electrode tip.

5. Rescanning the electrode as in Step 2 above.

For some electrodes, these steps were repeated several times for several electrodes. Using these procedures, the ultrasonic cleaning removed the mercury from the mercury thin-film electrodes in less than about 1 minute. The gold film electrodes showed that the plated gold could be "mostly" removed (at approximately 75-85%) after ultrasonic application lasting between from about 3 to about 15 minutes. Electrode position in the bath and depth of immersion affect the rate of gold removal.

After ultrasonic cleaning, mercury and gold electrodes were replated with a new thin-film metal and tested (no mechanical cleaning). These electrodes showed little degradation as indicated by a lack of increased background current (some increased background current was seen for gold electrodes). Each electrode type displayed typical sensitivity to target analyte metals in an ASV measurement. Lead was used as the target analyte for the mercury thin film electrodes and arsenic was the target analyte for the gold thin film electrode.

Flow cell ultrasonic cleaning. The method of the invention is applicable to electrodes housed in an electrochemical flow cell. Representative flow cells include flow cells useful in automated measurement of trace metals by stripping voltammetry techniques including ASV and CSV. Full automation of these measurements requires avoiding removal of the working electrode from the cell for occasional mechanical cleaning. The present invention provides a fully automated, in place, ultrasonic cleaning step as part of a complete working electrode reconditioning scheme.

In a further aspect, the invention provides an assembly comprising an ultrasonic device in sonic communication with an electrochemical cell. The ultrasonic device includes a housing; an ultrasound generator for generating ultrasonic energy; an ultrasonic window for coupling the ultrasonic energy into the flow cell; and a chamber defined by the housing, ultrasound generator, and ultrasonic window for receiving a liquid to provide a reservoir. The electrochemical cell includes a flow cell having a sample volume for receiving a liquid sample, the sample volume in communication with a sample inlet and sample outlet, wherein the sample volume is defined by the flow cell and the ultrasonic window; and a working electrode in liquid communication with the liquid sample for measuring the concentration of a metal in the liquid sample.

Figure 2:
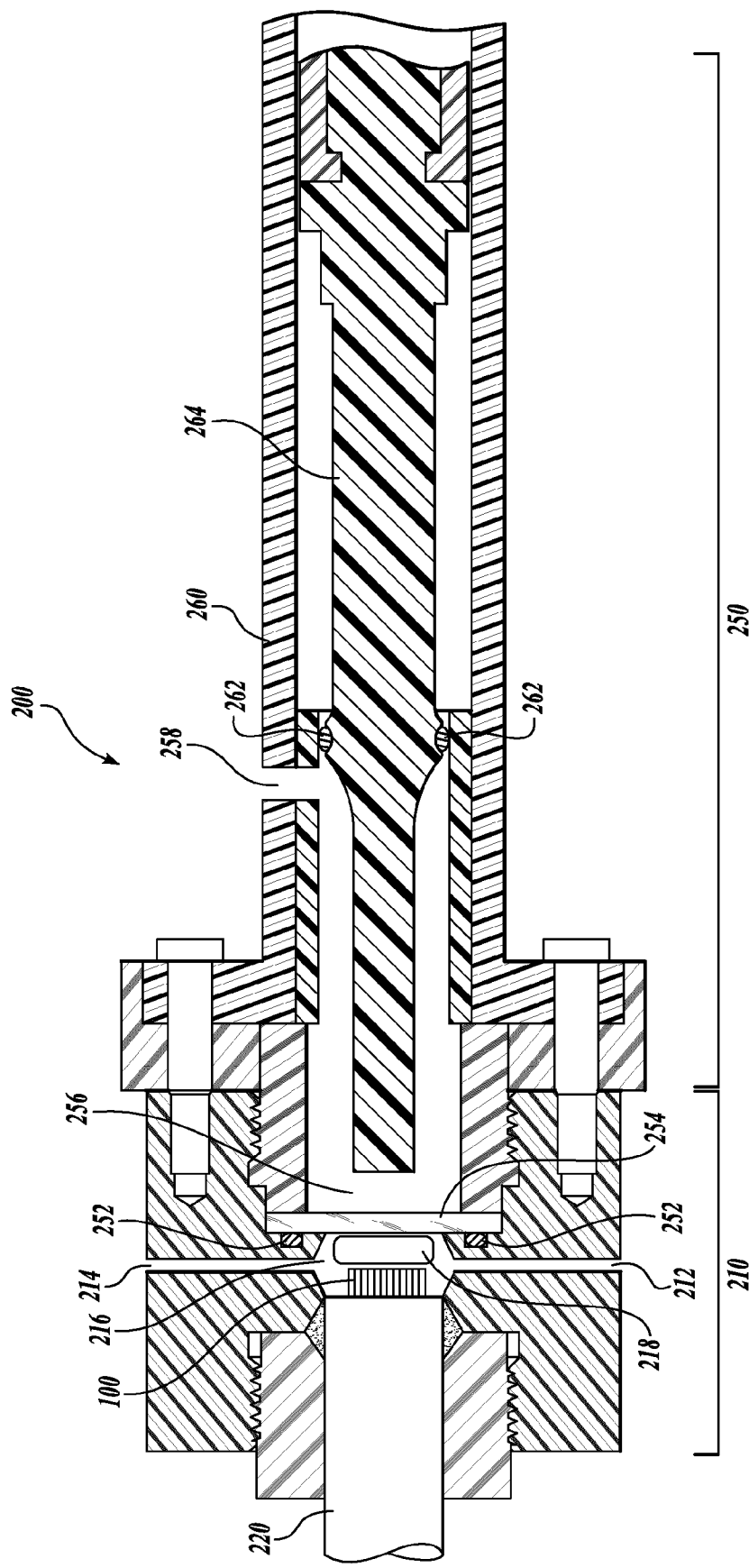
FIG. 2 is a schematic illustration of a representative assembly of the invention comprising an ultrasonic device in sonic communication with an electrochemical cell, the ultrasonic device is affixed to the cell, ultrasonic energy is coupled into the cell through an ultrasonic window.

A representative assembly comprising an ultrasonic device in sonic communication with an electrochemical cell for conducting trace metal measurements and that includes an ultrasonic generator for ultrasonic electrode cleaning is illustrated in FIG. 2. Referring to FIG. 2, assembly 200 includes electrochemical flow cell 210 affixed to ultrasonic device 250. Flow cell 210 is in sonic communication with ultrasonic device 250 through ultrasonic window 254. As used herein, the phrase "sonic communication" refers to the communication of ultrasonic energy from an ultrasound generator to another object. In the practice of the method of the invention, ultrasound generator (horn 264) is in sonic communication with flow cell sample volume 216 and electrode 100 through window 254.

Ultrasonic device 250 includes housing 260, ultrasound generator 264 for generating ultrasonic energy (ultrasonic transducer for driving the ultrasonic generator is not shown), ultrasonic window 254 for coupling the ultrasonic energy into the flow cell, and chamber 256 defined by housing 260, ultrasound generator 264 secured and sealed by o-ring 262, and ultrasonic window 254. In the practice of the method of the invention, chamber 256 is filled with a liquid (e.g., water) through port 258 to form a reservoir, which places ultrasound generator 264 in liquid communication with window 254 during ultrasonic cleaning of electrode 100.

Electrochemical cell 210 includes a flow cell having sample volume 216 for receiving a liquid sample, the sample volume in liquid communication with sample inlet 212 and sample outlet 214. Sample volume 216 is defined by the flow cell, including electrode 100 and its housing 220, and ultrasonic window 254. Stir bar 218 may be positioned in the sample volume and stirred during use. Electrochemical cell 210 includes a working electrode (e.g., electrode 100) in liquid communication with the liquid sample containing a concentration of a metal to be measured. It will be appreciated that the electrochemical cell includes a reference electrode and may optionally include an auxiliary electrode. The nature and type the electrodes utilized in the electrochemical cell will depend on the electrochemical technique being employed (e.g., amperometry, potentiometry, direct voltammetry, cyclic voltammetry). Only the working electrode is illustrated in FIG. 2. O-ring 252 assists in sealing ultrasonic device 250 to electrochemical cell 210. In the practice of the method of the invention, sample volume 216 is filled with a liquid (e.g., water) to form a reservoir, which places window 254 in liquid communication with electrode 100 during ultrasonic cleaning of electrode 100.

The representative flow cell illustrated in FIG. 2 has an internal volume of approximately 1 mL and includes an electrode array (e.g., NANO-BAND electrode) having an 0.5 inch outside diameter.

In the methods of the invention, ultrasonic cleaning is performed by sonication provided by an ultrasonic generator. In one embodiment, the ultrasonic generator is an ultrasonic horn.

Ultrasonic horns useful in the method of the invention include commercially available ultrasonic horns. Representative commercially available ultrasonic horns include a variable power unit (20 to 100 W) (total power dissipated by the unit, not delivered acoustical power) operating at 30 kHz (Dr. Hielscher GmbH, Warthestrasse 21, D-14513, Teltow, Germany), and a variable power unit (0 to 130 W) (total power dissipated by the unit, not delivered acoustical power) operating at 20 kHz (Sonics & Materials, Inc., Newtown, Conn.).

The ultrasonic horn is affixed to the flow cell along with a working electrode (e.g., NANO-BAND electrode) as shown in FIG. 2. The design illustrated in FIG. 2 allows for a variety of ultrasonic window materials. Representative windows include, for example, quartz windows having a thickness of about 0.008 inch, as well as other glasses and plastics such as TEFLON, PVDF, and polycarbonate. Suitable window materials include relatively hard and relatively thin plastic windows that are chemically inert, and relatively thin glass that is crack resistant. In one embodiment, the flow cell can be fabricated from these plastic materials and incorporate the window as a part of the cell, eliminating the need of a fitting for the window.

Experiments using the 20 to 100 W horn at 50 W and 100 W demonstrated that gold thin-films can be easily removed in approximately 3 minutes (gold removal greater than 75%). For this level of removal, water in the flow cell and the horn reservoir was kept at a temperature near room temperature. If the water temperature is increased, then the cleaning time for >75% removal rapidly increases. For example, for a hot flow cell (hot to the touch) more than fifteen minutes is sometimes required to remove more than 75% of the gold film. While room temperature (about 25 C) water works well, 45 C water does not. Actual water temperature at the tip of the ultrasonic horn is unknown, these temperatures pertain to the average water temperature in the ultrasonic chamber. Also, recirculating ice water into the ultrasonic chamber (20 mL volume) with a pump running at 16 mL/minute also works well.

By the method of the invention, gold thin films can be removed from gold and carbon electrodes with equal facility. The process is readily repeatable. For example, in accordance with the method of the invention, a gold film from a gold electrode was deposited and removed fifteen (15) times. The capacitive current of the electrode was successfully reduced to pre-thin film levels by ultrasonic cleaning, and after fifteen thin-film plating/removal cycles, 100 ppb arsenic in a 2 M HCl solution was readily measured by the electrode. It was observed that the electrodes appeared clean after the ultrasonic treatment with no visible pitting or removal epoxy from between the glass substrate and cover slip. Furthermore, no degradation in the background current of the electrode was observed (as measured by a staircase waveform made between −400 mV to +650 mV in 5 mV steps in a 2 M HCl solution).

Experiments using the 0 to 130 W horn at approximately one-tenth full power and a 0.020 inch thick PVDF ultrasonic window showed that not only could the thin-film mercury be successfully removed ultrasonically, but the thin film could be re-applied and accurate measurements (errors within +/−20%) of both lead and copper could be made. This process can be repeated at least 20 times with no change in measurement accuracy (measurements are made using anodic stripping voltammetry and the method of standard additions by which the treated sample is scanned, yielding a peak-height for each metal) and then known amounts of lead and copper are injected directly into the flow cell and the enhanced sample scanned after each addition. Correlating the increase in peak height for each metal with the known amount of each metal added to the flow cell comprises a single measurement of the original sample.

In one embodiment, a custom ultrasonic horn made from aluminum (or other metal) is used in combination with commercially available ultrasonic transducers. Such a custom horn could be shaped differently from the horn in illustrated in FIG. 2. The horn can be affixed directly to the window.

Custom could mean any of the following: better or different seal (as opposed to the o-ring 262 shown in FIG. 2), the shape of the tip could be made something other than flat if it is not attached to the ultrasonic window, the cross-section of the tip could be something other than round (an oval might made more sense because our NANO-BAND electrode is long and skinny), the size of the horn tip could be changed, the length of the horn could be changed and the resonant frequency of the horn could be changed.

In one embodiment, the ultrasonic horn is in contact with the window through an intermediate material (e.g., adhesive).

For cleaning (regenerating) a thin film mercury carbon NANO-BAND electrode, a 130 W horn at approximately one-tenth full power can be used. However, the power required depends very strongly on the thickness and material of the ultrasonic window. For example, a 0.020 inch thick glass requires about 3× more power than 0.008 inch thick glass, and 0.020 inch thick plastic (PVDF) requires about 3× more power than the same thickness glass. Furthermore, the 130 W rating on the ultrasonic horn pertains to the total power dissipated by the entire unit when operating at full power. One estimate suggests that the minimum acoustic power that must be delivered to the outside of the ultrasonic window is on the order of 0.2-1.0 W. The required power will also vary with the frequency of the acoustic energy. (the Sonics & Material unit uses 20 kHz sound waves).

In one embodiment, the ultrasonic generator is a megasonic generator. The term "megasonic" refers to very high ultrasonic frequency and typically implies a frequency greater than about 300 kHz. The use of very high frequency allows for a significant reduction in the size of the transducer and ultrasonic generator allowing for the reliable cleaning of small particles. A common frequency for megasonic transducers is about 1.5 MHz. At this frequency, the flow cell may act as a resonant cavity because its dimensions are only a few wavelengths in extent. The resonant frequency of the transducer assembly as well as the (potential) resonant loading of the flow cell are taken into consideration in designing flow cell/ultrasonic generator systems.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for regenerating a working electrode in an electrochemical cell, said electrochemical cell being housed in an assembly comprising an ultrasonic device in sonic communication with a working electrode, said ultrasonic device comprising an ultrasound generator for generating ultrasonic energy, and an ultrasonic window configured to couple the ultrasonic energy into a flow cell:
the electrochemical cell comprising:
the flow cell having a sample volume for receiving a liquid sample, the sample volume in communication with a sample inlet and sample outlet, wherein the sample volume is defined by the flow cell and the ultrasonic window; and
a working electrode in liquid communication with the sample volume;
the method comprising the steps of:
(a) applying ultrasonic energy to a working electrode in an electrochemical cell, wherein the electrode has a surface comprising a metal film plated thereon, wherein the metal film is fouled by accumulated material thereby reducing the electrode's effectiveness, wherein the applied ultrasonic energy is sufficient to remove at least a portion of the fouled metal film to provide to an electrode surface for receiving a metal; and
(b) plating a metal on the electrode surface for receiving a metal to provide a metal film on the electrode surface, thereby regenerating the working electrode.

2. The method of claim 1, wherein the working electrode comprises gold, iridium, platinum, carbon, glassy carbon, or diamond.

3. The method of claim 1, wherein the metal film comprises gold, bismuth, copper, silver, or mercury.

4. The method of claim 1, wherein the working electrode is at least one of a disk electrode, a microelectrode, an electrode array of microelectrodes, or a printed electrode.

5. The method of claim 1, wherein the working electrode is suitable for measuring the concentrations of trace metals by stripping voltammetry.

6. The method of claim 1, wherein the electrochemical cell is a flow cell.

7. The method of claim 1, wherein regenerating the working electrode is performed intermediate measuring trace element concentrations using the electrode.

8. The method of claim 7, wherein regenerating the working electrode is performed automatically.

9. The method of claim 1, wherein the ultrasonic energy is generated by an ultrasonic horn.

10. The method of claim 9, wherein the ultrasonic horn is in sonic communication with the working electrode.

11. The method of claim 1, wherein the ultrasonic energy is applied in the megasonic frequency range.

12. A method for measuring the concentration of a metal in a liquid sample in an electrochemical cell, said electrochemical cell being housed in an assembly, comprising an ultrasonic device in sonic communication with a working electrode, said ultrasonic device corn ricin an ultrasound generator for generating ultrasonic energy, and an ultrasonic window configured to couple the ultrasonic energy into a flow cell;
the electrochemical cell comprising:
the flow cell having a sample volume for receiving a liquid sample, the sample volume in communication with a sample inlet and sample outlet, wherein the sample volume is defined by the flow cell and the ultrasonic window; and
the working electrode in liquid communication with the sample volume;
the method comprising the steps of:
(a) introducing a first liquid sample containing a measurable quantity of a metal into the electrochemical cell;
(b) measuring the concentration of the metal in the first sample electrochemically;
(c) exiting the first liquid sample from the electrochemical cell;

(d) introducing a cleaning liquid into the electrochemical cell;

(e) applying ultrasonic energy to the working electrode, wherein the applied ultrasonic energy is sufficient to remove at least a portion of accumulated material from the working electrode surface thereby regenerating the working electrode;

(f) introducing a second liquid sample containing a measurable quantity of a metal into the electrochemical cell; and (g) measuring the concentration of the metal in the second sample electrochemically.

13. The method of claim 12, wherein the cleaning liquid is water.

14. The method of claim 12, wherein the working electrode comprises gold, iridium, platinum, carbon, glassy carbon, or diamond.

15. The method of claim 12, wherein the working electrode is at least one of a disk electrode, a microelectrode, an electrode array of microelectrodes, or a printed electrode.

16. The method of claim 12, wherein the ultrasonic energy is generated by an ultrasonic horn.

17. The method of claim 12, wherein the working electrode has a surface further comprising a metal film plated thereon.

18. The method of claim 17, wherein the applied ultrasonic energy is sufficient to remove at least a portion of the metal film to provide to a working electrode surface for receiving a metal.

\* \* \* \* \*